(12) United States Patent
Meyer et al.

(10) Patent No.: US 10,324,594 B2
(45) Date of Patent: Jun. 18, 2019

(54) ENTERPRISE PROTOCOL MANAGEMENT

(71) Applicant: Siemens Healthcare GmbH, Erlangen (DE)

(72) Inventors: Heiko Meyer, Uttenreuth (DE); Jacob Stolk, Salt Lake City, UT (US); Vibhas S. Deshpande, Austin, TX (US); Keith Aaron Heberlein, Charlestown, MA (US); Peter Kollasch, Minnetonka, MN (US); Abraham Padua, Jr., Houston, TX (US); Dieter Faust, Erlangen (DE); Lars Lauer, Neunkirchen (DE)

(73) Assignee: Siemens Healthcare GmbH, Erlangen (DE)

( * ) Notice: Subject to any disclaimer, the term of this patent is extended or adjusted under 35 U.S.C. 154(b) by 390 days.

(21) Appl. No.: 14/927,640

(22) Filed: Oct. 30, 2015

(65) Prior Publication Data

US 2017/0123612 A1 May 4, 2017

(51) Int. Cl.
*G06F 3/0484* (2013.01)
*G16H 40/40* (2018.01)
(Continued)

(52) U.S. Cl.
CPC ............ *G06F 3/0484* (2013.01); *A61B 5/055* (2013.01); *A61B 5/7435* (2013.01); *A61B 6/545* (2013.01);
(Continued)

(58) Field of Classification Search
CPC .... G06F 3/0484; G06F 3/0412; G06F 3/0481; G06F 3/14
See application file for complete search history.

(56) References Cited

U.S. PATENT DOCUMENTS

| 7,865,475 B1 * | 1/2011 | Yadav | G06F 11/2069 |
| | | | 707/655 |
| 2002/0143575 A1 * | 10/2002 | Hansen | G06F 19/321 |
| | | | 705/2 |

(Continued)

FOREIGN PATENT DOCUMENTS

WO 2015121301 A1 8/2015

OTHER PUBLICATIONS

EP Search report in EP Application No. 16194604.1, dated Mar. 21, 2017.

*Primary Examiner* — Anil K Bhargava

(57) ABSTRACT

A system for generating medical image scanner configurations includes a scanner configuration database and a simulation component. The database stores a scanner configuration dataset corresponding to a medical image scanner. The simulation component includes a display module which is configured to present a graphical user interface (GUI) utilized by the medical image scanner, and an editing module which is configured to create a modified scanner configuration dataset based on commands received from a user via the GUI. Additionally, the simulation component includes a simulation module which is configured to (i) perform a simulation of the medical image scanner using the modified scanner configuration dataset to yield simulated results, (ii) use the display module to present the simulated results in the GUI, and (iii) in response to receiving user approval of the simulated results via the GUI, save the modified scanner configuration dataset to the database.

16 Claims, 4 Drawing Sheets

(51) Int. Cl.

| | | |
|---|---|---|
| *A61B 5/00* | (2006.01) | |
| *A61B 6/00* | (2006.01) | |
| *A61B 5/055* | (2006.01) | |
| *G01R 33/00* | (2006.01) | |
| *G01R 33/54* | (2006.01) | |
| *G06F 3/041* | (2006.01) | |
| *G06F 3/0481* | (2013.01) | |
| *G06F 3/14* | (2006.01) | |
| *G09B 19/00* | (2006.01) | |
| *G09B 23/28* | (2006.01) | |
| *G06F 19/00* | (2018.01) | |

(52) U.S. Cl.
CPC .............. *A61B 6/548* (2013.01); *A61B 6/563* (2013.01); *A61B 6/566* (2013.01); *A61B 6/58* (2013.01); *G01R 33/0064* (2013.01); *G01R 33/546* (2013.01); *G06F 3/0412* (2013.01); *G06F 3/0481* (2013.01); *G06F 3/14* (2013.01); *G09B 19/00* (2013.01); *G09B 23/286* (2013.01); *G16H 40/40* (2018.01); *A61B 2560/0271* (2013.01); *G06F 19/3418* (2013.01)

(56) References Cited

U.S. PATENT DOCUMENTS

| | | | |
|---|---|---|---|
| 2005/0063575 | A1 | 3/2005 | Ma et al. |
| 2006/0212727 | A1* | 9/2006 | Judge .................... G06F 1/3203 713/300 |
| 2007/0228137 | A1* | 10/2007 | Bhella .................. G06F 9/4411 235/375 |
| 2009/0113413 | A1 | 4/2009 | Reinz |
| 2011/0178384 | A1* | 7/2011 | Kuth ..................... A61B 5/0555 600/407 |
| 2013/0160000 | A1* | 6/2013 | Dominick ......... G06F 17/30312 718/1 |
| 2013/0176230 | A1* | 7/2013 | Georgiev .............. G08C 17/02 345/173 |

* cited by examiner

ENTERPRISE PROTOCOL MANAGEMENT

TECHNOLOGY FIELD

The present invention relates generally to methods, systems, and apparatuses related to creating, editing, and deploying image scanner configurations using a simulation component that emulates the physical scanner. The disclosed technology may be applied, for example, to generate scanner configuration datasets for Magnetic Resonance Imaging (MRI) scanners and/or scanners corresponding to other imaging modalities.

BACKGROUND

One of the big healthcare trends in the United States and worldwide is standardization of imaging procedures. There is also a trend towards integration of smaller healthcare practices into larger organizations which increases the demand for standardization. In turn, the implementation of standards becomes a bigger and bigger logistical challenge because the imaging devices may be geographically separated by hundreds of miles. One of the key challenges is to ensure that imaging data for a specific diagnostic question is acquired with the same imaging configuration (e.g., imaging parameters or protocols) throughout the whole hospital network. This is important, because the scanner configuration determines contrast and image quality, greatly influencing the ability to diagnose diseases reliably. Institutions are more and more asked to account for the quality of their service and reimbursements are increasingly linked to the diagnostic performance. Thus, maintaining the same image quality and contrast for a given diagnostic question is crucial to keep or even grow revenue from the examinations.

On the other hand, the imaging systems allow operators to freely select scanner configurations. In large hospitals and imaging networks, it cannot be guaranteed that all operators have the same level of experience and can accidentally change the scanner configuration to the worse and store those parameters. Subsequent scans will then all be done with these suboptimal settings. This may remain unnoticed for quite some time and correcting it requires a person to physically modify the imaging device and store the correct parameters. This is time-consuming, error-prone and will only be possible when the device is not otherwise being used (i.e., when no patients are being examined). Thus it interferes with the clinical workflow or requires the installation after hours.

SUMMARY

Embodiments of the present invention address and overcome one or more of the above shortcomings and drawbacks, by providing methods, systems, and apparatuses related to the remote creation, editing, and maintenance of configuration datasets associated with medical image scanners.

According to some embodiments, a system for generating medical image scanner configurations includes scanner configuration database and a simulation component. The scanner configuration database stores a scanner configuration dataset corresponding to a medical image scanner operating within a medical facility. The simulation component includes a display module, an editing module, and a simulation module. The display module is configured to present a graphical user interface (GUI) utilized by the medical image scanner. The editing module is configured to create a modified scanner configuration dataset based on one or more commands received from a user via the GUI. The simulation module is configured to (i) perform a simulation of the medical image scanner using the modified scanner configuration dataset to yield simulated results, (ii) use the display module to present the simulated results in the GUI, and (iii) respond to receiving user approval of the simulated results via the graphical user interface, save the modified scanner configuration dataset to the scanner configuration database.

In some embodiments of the aforementioned system, the system further comprises a scanner interface component which is configured to transfer the modified scanner configuration dataset from the scanner configuration database to the medical image scanner. This scanner interface component may be configured to transfer the modified scanner configuration dataset from the scanner configuration database to the medical image scanner via any data transfer method known in the art including, for example, services such as electronic mail. In some embodiments, the scanner interface component is configured to automatically transfer the modified scanner configuration dataset from the scanner configuration database to the medical image scanner at a pre-determined time (e.g., at a particular time of day, during off-peak usage hours, during scanner startup, or during scanner shutdown). Additionally, in some embodiments, the scanner interface component is configured to facilitate transfer of the current scanner configuration dataset from the medical image scanner to the scanner configuration database.

The system configuration database used in the aforementioned system may have additional features or refinements in different embodiments of the present invention. For example, in some embodiments, the database is located on the medical image scanner and the simulation component is executed by a computing device within the medical image scanner. In other embodiments, the database is located on a server connected to the medical image scanner via a computer network and the simulation component is executed by the server. Furthermore, in some embodiments, the scanner configuration database stores additional scanner configuration datasets corresponding to additional medical image scanners operating within the medical facility and the system further comprises additional simulation components, with each respective additional component corresponding to a distinct additional medical image scanner. In one embodiment, the system comprises virtual computers which are configured to execute the medical image scanner and the additional medical image scanners.

According to other embodiments, a method for generating medical image scanner configurations for medical image scanner systems operating within a medical facility includes identifying a medical image scanner operating within the medical facility. The medical image scanner comprises hardware configured to present a GUI allowing a user to specify a scanner configuration dataset for operating the medical image scanner. The scanner configuration dataset may include, for example, imaging protocols to be applied by the scanner and/or examination workflows to be applied on the scanner. The method further includes launching a simulation component which is configured to: display the GUI, present the scanner configuration dataset in the GUI, modify the scanner configuration dataset according to user commands received via the GUI to yield a user-specified scanner configuration dataset, executing a simulation of the medical image scanner using the user-specified scanner configuration dataset to yield simulated results, and receiving user approval of the simulated results. Then, in response to receiving user approval of the simulated results, the user-specified scanner configuration dataset is transferred to the medical image scanner. Similar to the techniques discussed with respect to the system for generating medical image scanner configurations, the method may transfer the user-specified scanner configuration dataset using any technique known in the art and may selectively transfer the dataset at pre-determined times (e.g., a system startup or shutdown).

According to other embodiments, a system for generating medical image scanner configurations includes a scanner configuration database and a plurality of simulation components. The scanner configuration database stores scanner configuration datasets corresponding to a plurality of medical image scanners operating within a medical facility. Each respective simulation component is configured to generate, based on user-supplied commands, a modified scanner configuration dataset corresponding to a distinct medical image scanner included in the plurality of medical image scanners. Each simulation component is also configured to (i) simulate hardware corresponding to the distinct medical image scanner using the modified scanner configuration dataset to yield simulated results and (ii) in response to receiving user approval of the simulated results, transfer the modified scanner configuration dataset to the distinct medical image scanner. In some embodiments, the aforementioned system also includes a plurality of virtual computers, each of which is configured to execute one of the plurality of simulation components.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION OF ILLUSTRATIVE EMBODIMENTS

The following disclosure describes the present invention according to several embodiments directed at methods, systems, and apparatuses related to creating, editing, and deploying image scanner configurations using a simulation component that emulates the physical scanner. This simulation component, referred to herein as a "simulator" may be deployed either locally (i.e., within the enterprise which owns the medical image scanners) and/or in a cloud-based environment outside of the enterprise. The simulator solution can support multiple scanner configurations with different hardware and software options, for example, using separate computers or separate virtual computers. Additionally, in some embodiments, each computer or virtual computer has boot options that allow it to toggle between different medical image scanners.

Figure 1:
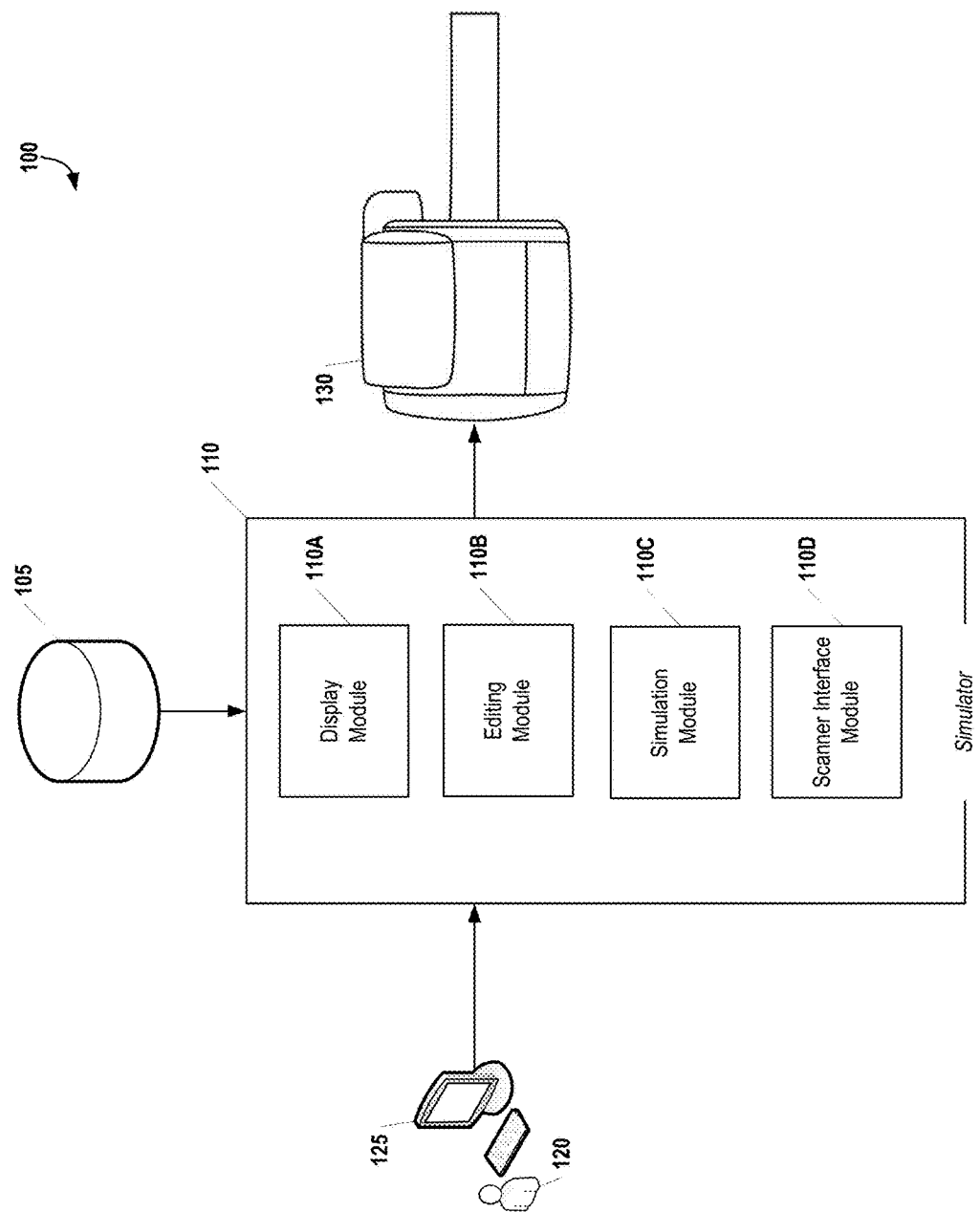
FIG. 1 illustrates a system for generating configurations for a Medical Image Scanner, according to some embodiments.

FIG. 1 illustrates a system 100 for generating configurations for a Medical Image Scanner 130, according to some embodiments. The system 100 illustrated in FIG. 1 uses simulation components or "simulators" for enterprise management of protocols. The term "simulator," as used herein, refers to software that operates the user interface of an imaging device without actual imaging hardware (e.g., magnets, control system, reconstruction hardware). A simulator mimics the operation of a real scanner with the primary difference being that no control commands are sent to the hardware and no image data is acquired. This allows imaging parameters, protocols and acquisition workflows to be edited, set up, and stored in the same manner as on a real, physical system. The system 100 may also allow the import of protocols from systems within the fleet to analyze the current status of the protocols and use them as a basis for modifications. It also may allow the export of the protocols (e.g., single protocols and whole examination programs or workflows) to be later (re-)deployed across a fleet.

In the example of FIG. 1, Simulator 110 simulates the hardware associated with a Medical Image Scanner 130. In some embodiments, the Simulator 110 is located on the Medical Image Scanner 130 and is included by a computing device within the Medical Image Scanner 130. In other embodiments, the Simulator 110 is executed on a server connected to the Medical Image Scanner 130 via a computer network (not shown in FIG. 1). The Simulator 110 may correspond to one medical image scanner or, alternatively, a group of medical image scanners. For example, in some embodiments, the Simulator 110 comprises software which mimics a real scanner. In such embodiments, the Simulator 110 may be configured to export settings, for example, onto a hard disk in the network. The import of the settings may be handled separately. In other embodiments, the Simulator 110 comprises software which includes a plurality of different scanner configurations. In these embodiments, the Simulator 110 may be configured to establish a connection to the individual physical systems in the enterprise to read and write the parameter settings.

In the example of FIG. 1, the Simulator 110 comprises four sub-components: a Display Module 110A, an Editing Module 110B, a Simulation Module 110C, and a Scanner Interface Module 110D.

The Display Module 110A is configured to present a graphical user interface utilized by the Medical Image Scanner 130 on the User Computer 125 for viewing by User 120. More specifically, Medical Image Scanner 130 includes a computer which allows operators to interface with the scanner hardware. The Display Module 110A is configured to mimic the specific interface associated with the Medical Image Scanner 130. Thus, the graphical user interface displayed to the User 120 on the User Computer 125 will look identical to that presented to the operator of the Medical Image Scanner 130. The Display Module 110A may use any technique known in the art for providing the graphical user interface to the User Computer 125. For example, in some embodiments, the Display Module 110A is configured to create a webpage with interface components. This webpage may then be viewed by the User 120 via a standard web browser on the User Computer 125. Note that this allows flexibility in the type of computing device that may be used as a User Computer 125. Thus, although a desktop computer is shown in the example of FIG. 1, a smartphone, a tablet, or any other computing device generally known in the art capable of displaying interactive webpages may be used as the User Computer 125.

The Editing Module 110B allows the User 120 to create a customized scanner configuration dataset based on one or more commands received from a user via the graphical user interface. The contents of the scanner configuration dataset will depend on the modality of the Medical Image Scanner 130. For example, in the context of Magnetic Resonance Imaging (MRI) the scanner configuration dataset may comprise a set of imaging parameters that specify how data should be acquired (e.g., pulse sequences) and image reconstruction data (e.g., reconstruction algorithms and their respective parameters). Additionally, in some embodiments, the Editing Module 110B can also be configured to keep track of the software options that are available on a specific medical image scanner in the enterprise (e.g., hospital) and automatically only offer the parameters which are available on this particular scanner.

The Editing Module 110B is operably coupled to a Scanner Configuration Database 105 which stores one or more pre-existing scanner configuration datasets corresponding to a Medical Image Scanner 130. In some embodiments, the Scanner Configuration Database 105 stores additional scanner configuration datasets corresponding to additional medical image scanners operating within the medical facility (not shown in FIG. 1). The system 100 may also include additional simulators similar to Simulator 110, corresponding to each additional scanner.

Once the Editing Module 110B retrieves a scanner configuration dataset from the Scanner Configuration Database 105, it communicates with Display Module 110A to present the scanner configuration dataset within the interface presented on the User Computer 125. The User 120 can then edit the dataset as desired. The User Computer 125 then delivers the modified scanner configuration dataset back to the Simulator 110.

Upon receipt of the modified scanner configuration dataset, the Simulation Module 110C performs a simulation of the Medical Image Scanner 130 using the dataset to yield simulated results. The Simulation Module 110C then utilizes the Display Module 110A to present the simulated results in the graphical user interface on the User Computer 125. The User 120 can then view the results and indicate acceptance or rejection. If the User 120 rejects the results, the Editing Module 110B may again present the User 120 with the dataset to facilitate further editing. Then, the simulation process may be repeated. Once the User 120 indicates acceptance of the simulated results, the Simulation Module 110C saves the modified scanner configuration dataset to the Scanner Configuration Database 105.

The Scanner Interface Module 110D is configured to transfer the modified scanner configuration dataset from the Scanner Configuration Database 105 to the Medical Image Scanner 130. Various techniques may be applied for performing the data transfer between the Scanner Configuration Database 105 and the Medical Image Scanner 130. For example, in one embodiment, the Scanner Interface Module 110D is configured to transfer the modified scanner configuration dataset over a computer network (e.g., the Intranet or Internet) using via electronic mail. In other embodiments, other data transfer techniques may be used such as, without limitation, file transfer protocol (FTP) or direct communication techniques (e.g., USB).

In some embodiments, the Scanner Interface Module 110D is configured to automatically transfer the modified scanner configuration dataset from the scanner configuration database to the medical image scanner at a pre-determined time. This time may be set manually by the user or the time may be automatically selected. For example, in some embodiments, the time is selected to coincide with a known downtime of the Medical Image Scanner 130 (e.g., during overnight hours). In other embodiments, the Scanner Interface Module 110D may be configured to receive certain event messages from the Medical Image Scanner 130 (e.g., system startup, system shutdown, etc.). Based on these event messages, the Scanner Interface Module 110D may select the time for transferring the modified scanner configuration.

Figure 2:
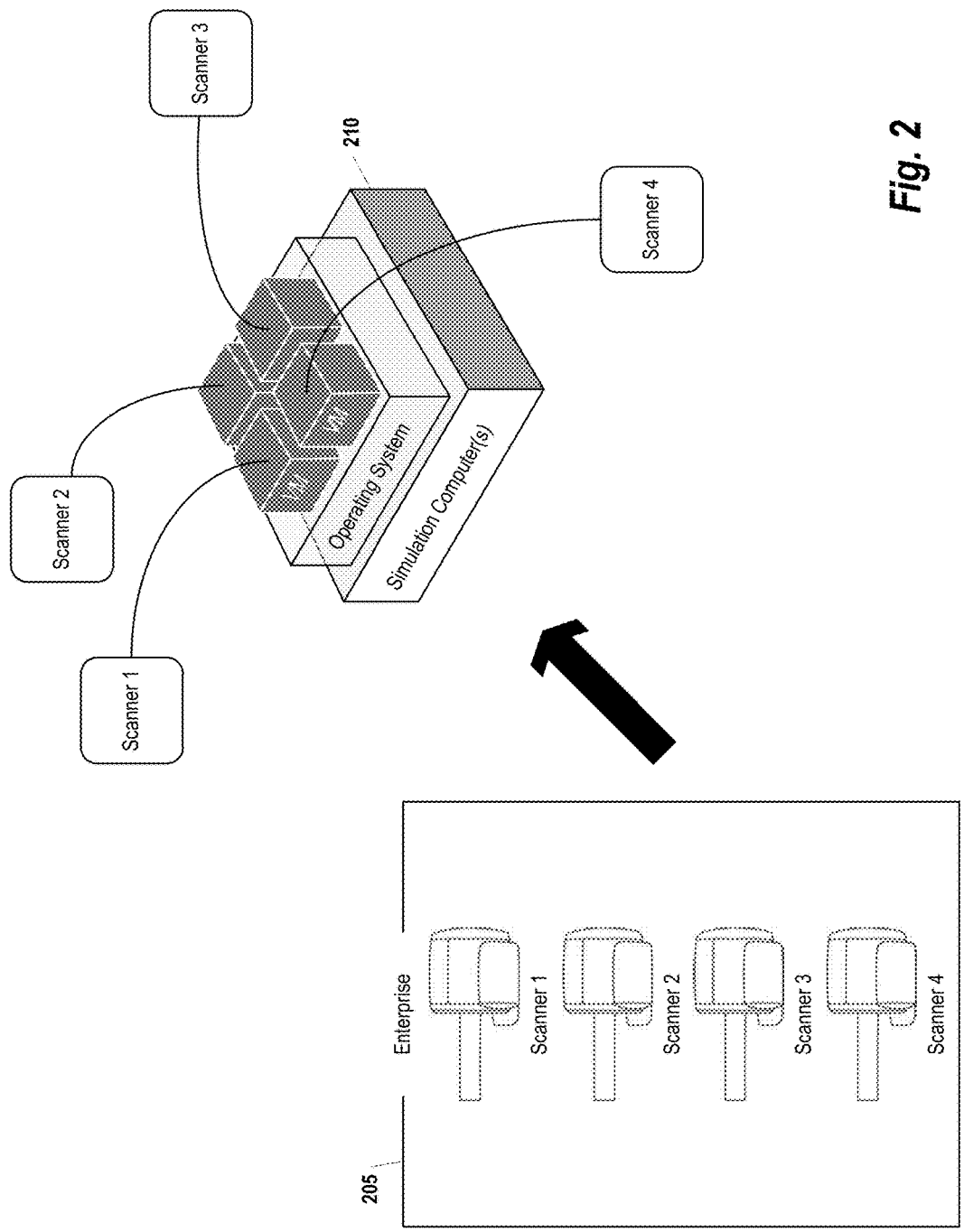
FIG. 2 provides an illustration how the system illustrated in FIG. 1 may be implemented to support an enterprise such as a hospital or chain of imaging providers, according to some embodiments.

FIG. 2 provides an illustration how the system 100 illustrated in FIG. 1 may be implemented to support an enterprise such as a hospital, according to some embodiments. In this example, the enterprise 205 has four medical image scanners. It should be noted that, although FIG. 1 illustrates the medical image scanners as MRI devices, the general concepts described in FIG. 2 may be extended to other enterprises with other types of devices, including those enterprises with a mix of different modalities.

Continuing with reference to FIG. 2, one or more simulation computers 210 are used to execute a simulator for each medical image scanner in the enterprise 205. The simulation computer(s) execute an operating system which provides basic computing functionality for the simulation computer(s) (i.e., functionality not specific to simulation purposes). In turn, the operating system executes a virtual machine (VM) for each scanner in the enterprise. The VM for a particular medical image scanner provides the simulator functionality for that medical image scanner. As is generally understood in the art, a VM is an application environment that emulates dedicated hardware. Thus, the VM associated with each medical image scanner can be used to emulate the application environment corresponding to its respective scanner. In this way one or more of the components illustrated in FIG. 1 may be implemented by each VM. For example, a VM may provide display, storage, editing, and simulation functionality for a particular medical image scanner. Then, to deliver the modified medical image dataset to the real-world hardware, one or more additional components (not shown in FIG. 2) may serve as an intermediary between each VM and its respective scanner.

It should be noted that VMs shown in FIG. 2 are only one technique that may be used in implementing the simulation computers For example, in other embodiments, a computer can be configured to resemble a specific scanner in the enterprise. So instead of multiple VMs, there may be a single system or VM, and when it connects to a specific scanner in the enterprise, it configures itself accordingly.

Figure 3:
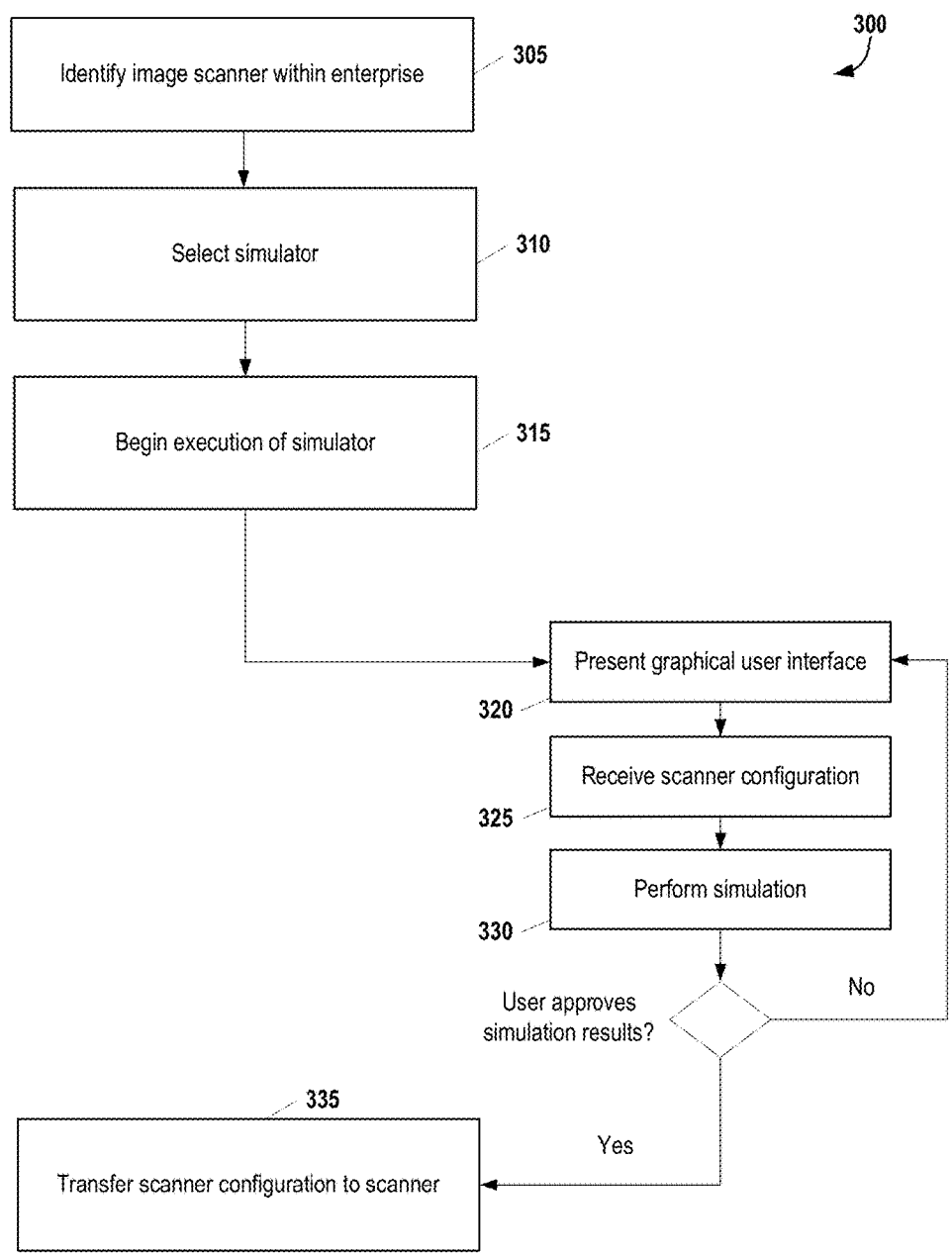
FIG. 3 illustrates a process for the creation and distribution of scanner configuration datasets, according to some embodiments.

FIG. 3 illustrates a process 300 for the creation and distribution of scanner configuration datasets, according to some embodiments. Starting at step 305, a particular image scanner is identified within the enterprise. This identification may be performed, for example, by a user interacting with a webpage or other interface providing a listing of available medical image scanners. Next, at step 310, the simulator corresponding to the identified medical image scanner is identified. In some embodiments, the association between the medical image scanner and the simulator may be pre-defined such that the user's identification of the scanner also selects the simulator. In other embodiments, the user's identification of the medical image scanner may be used to perform a look-up on the computer providing simulation functionality (see, e.g., FIG. 2). This look-up may be performed, for example, based on a model number or other identifier associated with the identified medical image scanner.

Continuing with reference to FIG. 3, at step 315 the execution of the simulator is initiated. As noted above with reference to FIG. 2, the simulator may be executed within a virtual machine. Alternatively, the simulator may be executed directly within the simulation computer's operating system. Steps 320-330 provide a high-level summary of the steps performed by the simulator. First, at step 320, the simulator presents a graphical user interface corresponding to the identified medical image scanner on the user's computer. In response, at step 325, a modified scanner configuration dataset is received from the user's computer. Then, at step 330, a simulation is performed using the modified configuration dataset. The results of the simulation are then presented to the user and the user has an opportunity to accept or reject the results. If the user rejects the results, steps 320-330 repeat, starting at step 320. However, if the user accepts the results, at step 335, the modified scanner configuration dataset used to generate the results is transferred to the corresponding medical image scanner. The process 300 may be utilized to provide custom scanner configurations to each medical image scanner with an enterprise.

The system and methods described herein may be used to facilitate the publication and peer-to-peer sharing of scanner configurations within and outside of the hospital network. In this way, the users can select optimal pre-existing configurations to apply to a particular clinical application. Additionally, the technology may be applied to share a user's preferred scanner configuration across different enterprises. For example, a doctor may travel between different medical facilities and desire application of a consistent scanner configuration. Moreover, because the simulation is performed without using the actual hardware, the technology described herein may be used to train individuals (e.g., students, application specialists, or technologists) in terms of protocol optimization and improving image quality.

Figure 4:
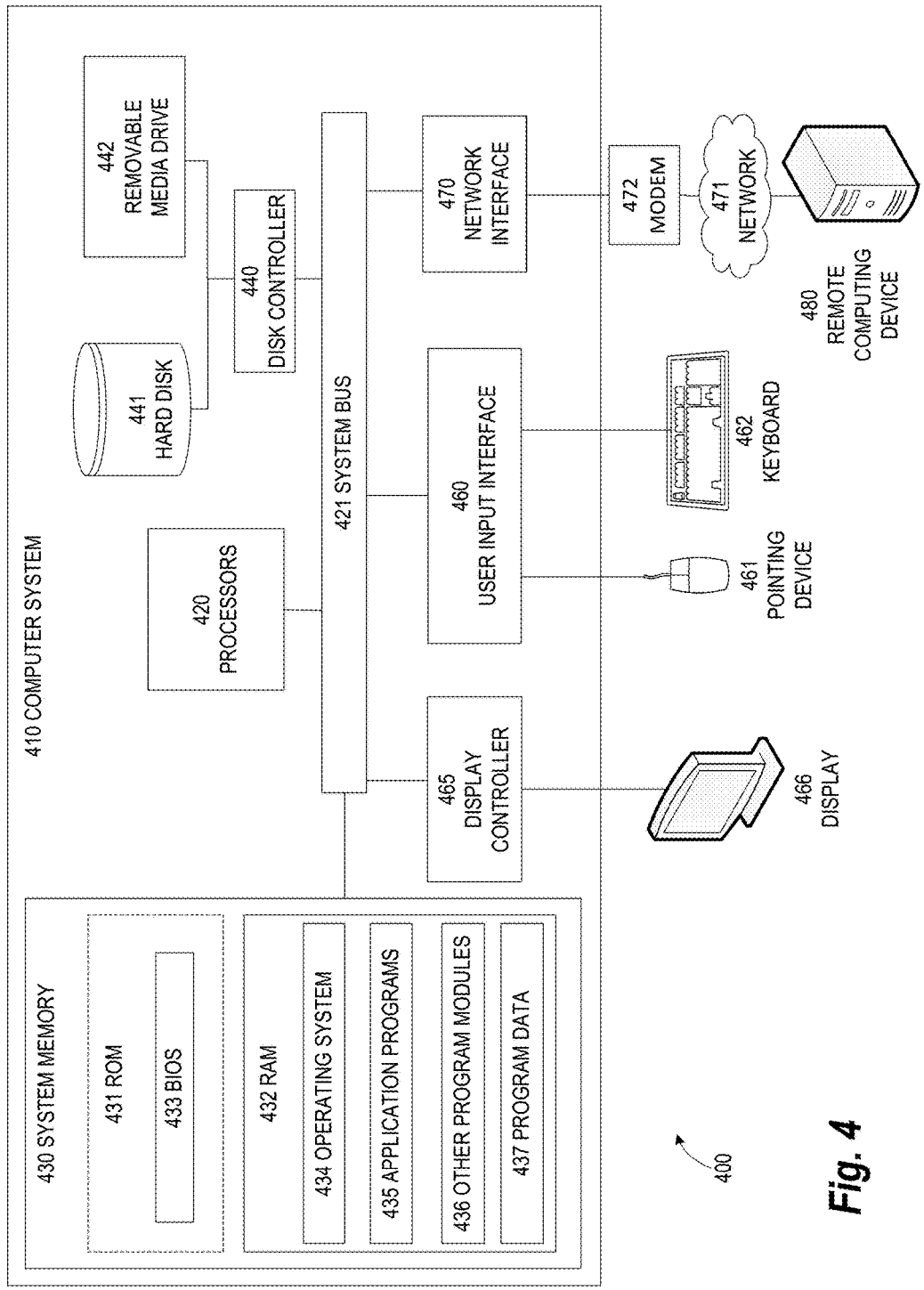
FIG. 4 illustrates an exemplary computing environment within which embodiments of the invention may be implemented.

FIG. 4 illustrates an exemplary computing environment 400 within which embodiments of the invention may be implemented. For example, this computing environment 400 may be used to implement the process 300 described above with respect to FIG. 3. In some embodiments, the computing environment 400 may be used to implement one or more of the devices illustrated in FIGS. 1 and 2. The computing environment 400 may include computer system 410, which is one example of a computing system upon which embodiments of the invention may be implemented. Computers and computing environments, such as computer system 410 and computing environment 400, are known to those of skill in the art and thus are described briefly here.

As shown in FIG. 4, the computer system 410 may include a communication mechanism such as a bus 421 or other communication mechanism for communicating information within the computer system 410. The computer system 410 further includes one or more processors 420 coupled with the bus 421 for processing the information. The processors 420 may include one or more central processing units (CPUs), graphical processing units (GPUs), or any other processor known in the art.

The computer system 410 also includes a system memory 430 coupled to the bus 421 for storing information and instructions to be executed by processors 420. The system memory 430 may include computer readable storage media in the form of volatile and/or nonvolatile memory, such as read only memory (ROM) 431 and/or random access memory (RAM) 432. The system memory RAM 432 may include other dynamic storage device(s) (e.g., dynamic RAM, static RAM, and synchronous DRAM). The system memory ROM 431 may include other static storage device(s) (e.g., programmable ROM, erasable PROM, and electrically erasable PROM). In addition, the system memory 430 may be used for storing temporary variables or other intermediate information during the execution of instructions by the processors 420. A basic input/output system (BIOS) 433 containing the basic routines that help to transfer information between elements within computer system 410, such as during start-up, may be stored in ROM 431. RAM 432 may contain data and/or program modules that are immediately accessible to and/or presently being operated on by the processors 420. System memory 430 may additionally include, for example, operating system 434, application programs 435, other program modules 436 and program data 437.

The computer system 410 also includes a disk controller 440 coupled to the bus 421 to control one or more storage devices for storing information and instructions, such as a hard disk 441 and a removable media drive 442 (e.g., floppy disk drive, compact disc drive, tape drive, and/or solid state drive). The storage devices may be added to the computer system 410 using an appropriate device interface (e.g., a small computer system interface (SCSI), integrated device electronics (IDE), Universal Serial Bus (USB), or FireWire).

The computer system 410 may also include a display controller 465 coupled to the bus 421 to control a display 466, such as a cathode ray tube (CRT) or liquid crystal display (LCD), for displaying information to a computer user. The computer system includes an input interface 460 and one or more input devices, such as a keyboard 462 and a pointing device 461, for interacting with a computer user and providing information to the processor 420. The pointing device 461, for example, may be a mouse, a trackball, or a pointing stick for communicating direction information and command selections to the processor 420 and for controlling cursor movement on the display 466. The display 466 may provide a touch screen interface which allows input to supplement or replace the communication of direction information and command selections by the pointing device 461.

The computer system 410 may perform a portion or all of the processing steps of embodiments of the invention in response to the processors 420 executing one or more sequences of one or more instructions contained in a memory, such as the system memory 430. Such instructions may be read into the system memory 430 from another computer readable medium, such as a hard disk 441 or a removable media drive 442. The hard disk 441 may contain one or more datastores and data files used by embodiments of the present invention. Datastore contents and data files may be encrypted to improve security. The processors 420 may also be employed in a multi-processing arrangement to execute the one or more sequences of instructions contained in system memory 430. In alternative embodiments, hard-wired circuitry may be used in place of or in combination with software instructions. Thus, embodiments are not limited to any specific combination of hardware circuitry and software.

As stated above, the computer system 410 may include at least one computer readable medium or memory for holding instructions programmed according to embodiments of the invention and for containing data structures, tables, records, or other data described herein. The term "computer readable medium" as used herein refers to any medium that participates in providing instructions to the processor 420 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 441 or removable media drive 442. Non-limiting examples of volatile media include dynamic memory, such as system memory 430. Non-limiting examples of transmission media include coaxial cables, copper wire, and fiber optics, including the wires that make up the bus 421. Transmission media may also take the form of acoustic or light waves, such as those generated during radio wave and infrared data communications.

The computing environment 400 may further include the computer system 410 operating in a networked environment using logical connections to one or more remote computers, such as remote computer 480. Remote computer 480 may be a personal computer (laptop or desktop), a mobile device, a server, a router, a network PC, a peer device or other common network node, and typically includes many or all of the elements described above relative to computer system 410. When used in a networking environment, computer system 410 may include modem 472 for establishing communications over a network 471, such as the Internet. Modem 472 may be connected to bus 421 via user network interface 470, or via another appropriate mechanism.

Network 471 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 410 and other computers (e.g., remote computer 480). The network 471 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 471.

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112, sixth paragraph, unless the element is expressly recited using the phrase "means for."

We claim:

1. A system for generating medical image scanner configurations, the system comprising:
   a scanner configuration database storing a scanner configuration dataset corresponding to a medical image scanner operating within a medical facility; and
   a virtual machine that emulates an application environment of the medical image scanner, the application environment comprising a plurality of hardware components, wherein the virtual machine executes:
      a display module configured to present a graphical user interface that emulates a user interface utilized by the medical image scanner, wherein the graphical user interface is identical to the user interface utilized by the medical image scanner,
      an editing module configured to create a modified scanner configuration dataset based on one or more commands received from a user via the graphical user interface, a simulation module configured to (i) perform a simulation of the medical image scanner using the modified scanner configuration dataset to yield simulated results, (ii) use the display module to present the simulated results in the graphical user interface, and (iii) in response to receiving user approval of the simulated results via the graphical user interface, save the modified scanner configuration dataset to the scanner configuration database, wherein the scanner configuration database is located on the medical image scanner and the virtual machine is executed by a computing device within the medical image scanner.

2. The system of claim 1, further comprising:

a scanner interface component configured to transfer the modified scanner configuration dataset from the scanner configuration database to the medical image scanner.

3. The system of claim 2, wherein the scanner interface component is configured to transfer the modified scanner configuration dataset via electronic mail from the scanner configuration database to the medical image scanner.

4. The system of claim 2, wherein the scanner interface component configured to automatically transfer the modified scanner configuration dataset from the scanner configuration database to the medical image scanner at a pre-determined time.

5. The system of claim 2, wherein the scanner interface component configured to automatically transfer the modified scanner configuration dataset from the scanner configuration database to the medical image scanner based on an indication that the medical image scanner has performed a startup operation.

6. The system of claim 2, wherein the scanner interface component configured to automatically transfer the modified scanner configuration dataset from the scanner configuration database to the medical image scanner based on an indication that the medical image scanner has performed a shutdown operation.

7. The system of claim 1, further comprising:

a scanner interface component configured to transfer the scanner configuration dataset from the medical image scanner to the scanner configuration database.

8. The system of claim 1, wherein the scanner configuration database stores additional scanner configuration datasets corresponding to additional medical image scanners operating within the medical facility and the system further comprises a plurality of additional virtual machines, each respective additional virtual machine corresponding to a distinct additional medical image scanner.

9. A system for generating medical image scanner configurations, the system comprising:

a scanner configuration database storing a scanner configuration dataset corresponding to a medical image scanner operating within a medical facility; and a virtual machine that emulates an application environment of the medical image scanner, the application environment comprising a plurality of hardware components, wherein the virtual machine executes:

a display module configured to present a graphical user interface that emulates a user interface utilized by the medical image scanner, wherein the graphical user interface is identical to the user interface utilized by the medical image scanner, an editing module configured to create a modified scanner configuration dataset based on one or more commands received from a user via the graphical user interface, a simulation module configured to (i) perform a simulation of the medical image scanner using the modified scanner configuration dataset to yield simulated results, (ii) use the display module to present the simulated results in the graphical user interface, and (iii) in response to receiving user approval of the simulated results via the graphical user interface, save the modified scanner configuration dataset to the scanner configuration database, wherein the scanner configuration database is located on a server connected to the medical image scanner via a computer network and the virtual machine is executed by the server.

10. The system of claim 9, further comprising:

a scanner interface component configured to transfer the modified scanner configuration dataset from the scanner configuration database to the medical image scanner.

11. The system of claim 10, wherein the scanner interface component is configured to transfer the modified scanner configuration dataset via electronic mail from the scanner configuration database to the medical image scanner.

12. The system of claim 10, wherein the scanner interface component configured to automatically transfer the modified scanner configuration dataset from the scanner configuration database to the medical image scanner at a pre-determined time.

13. The system of claim 10, wherein the scanner interface component configured to automatically transfer the modified scanner configuration dataset from the scanner configuration database to the medical image scanner based on an indication that the medical image scanner has performed a startup operation.

14. The system of claim 10, wherein the scanner interface component configured to automatically transfer the modified scanner configuration dataset from the scanner configuration database to the medical image scanner based on an indication that the medical image scanner has performed a shutdown operation.

15. The system of claim 9, further comprising:

a scanner interface component configured to transfer the scanner configuration dataset from the medical image scanner to the scanner configuration database.

16. The system of claim 9, wherein the scanner configuration database stores additional scanner configuration datasets corresponding to additional medical image scanners operating within the medical facility and the system further comprises a plurality of additional virtual machines, each respective additional virtual machine corresponding to a distinct additional medical image scanner.

* * * * *